United States Patent [19]

Hill et al.

[11] Patent Number: 4,758,589
[45] Date of Patent: Jul. 19, 1988

[54] TETRAPHOSPHINE-COORDINATED GOLD(I) COMPLEXES

[75] Inventors: David T. Hill, North Wales; Randall K. Johnson, Ardmore, both of Pa.

[73] Assignee: SmithKline Beckman Corporation, Philadelphia, Pa.

[21] Appl. No.: 10,039

[22] Filed: Feb. 2, 1987

Related U.S. Application Data

[60] Division of Ser. No. 4,675,427, Jun. 23, 1987, which is a continuation-in-part of Ser. No. 736,001, May 20, 1985, abandoned.

[51] Int. Cl.[4] ............................................. A61K 31/28
[52] U.S. Cl. .................................................... 514/495
[58] Field of Search ......................................... 514/495

[56] References Cited

U.S. PATENT DOCUMENTS

| | | |
|---|---|---|
| 3,676,554 | 7/1972 | McGusty . |
| 3,718,680 | 2/1973 | McGusty . |
| 3,842,107 | 10/1974 | Sutton . |
| 3,842,108 | 10/1974 | Sutton . |
| 4,097,509 | 6/1978 | Schmidbaur et al. ............... 556/18 |
| 4,116,990 | 9/1978 | Budwick .............................. 556/18 |
| 4,186,064 | 1/1980 | Morrissey ........................... 556/18 |

FOREIGN PATENT DOCUMENTS

| | | |
|---|---|---|
| 0151046 | 8/1985 | European Pat. Off. . |
| 0164970 | 12/1985 | European Pat. Off. ............. 556/18 |

OTHER PUBLICATIONS

King et al., Inorg. Chem. vol. 10, No. 9, 1851–1860 (1971).
King et al., Inorg. Chem., vol. 10, No. 9, 1861–1867 (1971).
Mirabelli et al., Abstract #1194, Proceedings of AACR, 27 Mar. 1986.
Johnson et al., Abstract #1115, Proceedings of AACR 27, Mar. 1986.
Hill et al., Abstract #14, 190th American Chemial Society (1985).
Shaw et al., Inorganica Chimica Acta, 123, 213–216 (1986).
Eggleston et al., Inorganica Chimica Acta, 108, 221–226 (1985).
Mirabelli et al., Biochemical Pharmacology, 35(9), 1427–1433+1435–1443 (1986).
Mirabelli et al., J. Med. Chem., 29(2), 218–223 (1986).
Hill et al., Abstract #204, American Chemical Society.
Berners-Price et al., Abstract #244, American Chemical Society.
Johnson et al., Abstract #1115, Proceedings of AACR 27, Mar. 1986.
Hill et al., Abstract #14, 190th American Chemical Society.
Cariati et al., Inorg. Chim. Acta, 1(2), 315–18 (1967).
McAuliffe, J. C. S. Dalton, 1730–1735 (1979).
Bates et al., Inorg. Chim. Acta, 81(2), 151–156 (1984).
Kuhn et al., Chemiker-Zeitung, 105(3), 87–88 (1981).
Berners-Price et al., J. Chem. Soc. Dalton Trans, 969–974 (1984).
Struck et al., J. Med. Chem., 9, 414–417 (1966).
Mirabelli et al., Proceedings of AACR Mar. 1984, No. 1455 p. 367 (1984).
Mirabelli et al., Cancer Research, 45, 32–39 (1985).
Johnson et al., Proceedings of AACR Mar. 1985, No. 1001, p. 254 (1985).
Snyder et al., Proceedings of AACR Mar. 1985, No. 1007, p. 255 (1985).
Mirabelli et al., Proceedings of AACR Mar. 1985, No. 1008, p. 256 (1985).
Weinstock et al., J. Med. Chem., 17 (1), 139–140 (1974).

Primary Examiner—Jerome D. Goldberg
Attorney, Agent, or Firm—Carol G. Canter; Edward T. Lentz; Alan D. Lourie

[57] ABSTRACT

Tetraphosphine-coordinated gold (I) compounds, pharmaceutical compositions containing an effective, tumor cell growth-inhibiting amount of such a compound, and a method of treating tumor cells sensitive to such a compound which comprises administering a tumor cell growth-inhibiting amount of such a compound to an animal afflicted by said tumor cells.

10 Claims, No Drawings

TETRAPHOSPHINE-COORDINATED GOLD(I) COMPLEXES

CROSS-REFERENCES TO RELATED APPLICATIONS

This is a divisional of U.S. Pat. No. 4,675,427, issued June 23, 1987, which is a continuation-in-part of application Ser. No. 736,001, filed May 20, 1985 which is abandoned.

BACKGROUND OF THE INVENTION

This invention relates to novel tetraphosphine-coordinated gold(I) compounds which have tumor cell growth-inhibiting activity, pharmaceutical compositions containing an effective, tumor cell growth-inhibiting amount of such a novel compound, and a method for treating tumor cells sensitive to such a compound by administering tumor cell growth inhibiting amounts of such a novel compound to a host animal afflicted by such tumor cells.

The gold phosphine compounds of this invention are not known. Cariati et al., *Inorg. Chim. Acta*, 1(2), 315–18 (1967), and Bates et al., *Inorg. Chim. Acta*, 81(2), 151–156 (1984) disclose bis[1,2-bis(diphenylphosphino)ethane]gold(I) chloride. Struck et al., *J. Med. Chem.*, 9, 414–417 (1966), disclose cytotoxic activity for 1,2-bis(diphenylphosphino)ethane. None of the aforementioned references disclose or suggest the pharmaceutical compositions or methods of treatment of the instant invention.

SUMMARY OF THE INVENTION

This invention relates to novel gold phosphine compounds of the formula:

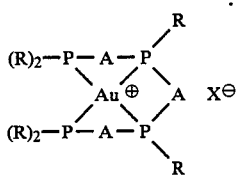

Formula (I)

wherein
R is the same and is phenyl;
A is the same and is a straight or branched alkanediyl chain of from one to six carbon atoms; and
X is halo.

This invention also relates to a pharmaceutical composition which comprises an effective tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of Formula (I).

Another aspect of this invention relates to a method of inhibiting the growth of animal tumor cells sensitive to a compound of Formula (I) which comprises administering to an animal afflicted with said tumor cells, an effective, tumor cell growth-inhibiting amount of a compound of Formula (I).

DETAILED DESCRIPTION OF THE INVENTION

All the compounds of Formula (I) can be prepared by methods available to one skilled in the art.

Generally, the compounds of Formula (I) can be prepared by reacting three moles of the appropriate tetraphos ligand of the following general structural formula:

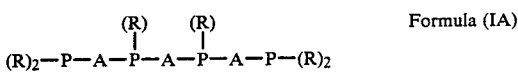

Formula (IA)

with one mole of the appropriate tetraphos-gold complex of the following general structural formula:

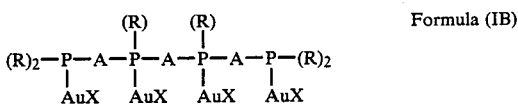

Formula (IB)

wherein R, X and A are as defined above, in a non-reactive organic solvent.

The necessary compounds of Formula (IA) are available from commercial sources, for example, from Strem Chemicals, Inc., Newburyport, Mass.

The necessary compounds of Formula (IB) can be prepared by reacting the appropriate compound of Formula (IA) with chloroauric acid tetrahydrate which has been reduced by treatment with thiodiglycol.

The compounds of Formula (IB) wherein X is bromo are prepared by reacting the appropriate compound of Formula (IA) with bromoauric acid hydrate (which is commercially available, for example from Strem Chemicals, Inc., Newburyport, Mass.) which has been reduced by treatment with thioglycol. Alternatively, the compounds of Formula (I) wherein X is bromo are prepared by reacting the appropriate compound of Formula (I), wherein X is chloro, with sodium bromide in an appropriate organic solvent, such as aqueous ethanol or DMF.

The compounds of Formula (I) wherein X is iodo are prepared by reacting the appropriate compound of Formula (I) wherein X is chloro or bromo with sodium iodide in an appropriate organic solvent, such as acetone.

As stated above, the compounds of Formula (I) have tumor cell growth-inhibiting activity which has been demonstrated in at least one animal tumor model.

P388 lymphocytic leukemia is currently the most widely used animal tumor model for screening for antitumor agents and for detailed evaluation of active compounds. This tumor system is widely accepted as an antitumor agent screening tool because it is sensitive to virtually all of the clinically active antineoplastic agents; quantitative and reproducible; amenable for large-scale screening; and predictive for activity in other animal tumor models. Drugs that are highly active in intraperitoneal (ip) P388 leukemia are generally active in other tumor models as well. The antitumor activity of the compounds of Formula (I) is demonstrated in the P388 leukemia mouse model employing the following protocol:

$10^6$ P388 leukemia cells are inoculated ip in B6D2F$_1$ mice. Twenty-four hours later, if the tumor inoculum proves to be free of bacterial contamination (as determined by 24 hours incubation in thioglycollate broth), animals are randomized into groups of 6 and housed in shoebox cages. The compound to be evaluated is dissolved in a minimal volume of N,N-dimethylacetamide (DMA). An equal volume of saline is added; if the drug comes out of solution an equal volume of polyethoxylated castor oil is added and then saline qs to a concentration such that the desired dose is delivered in 0.5 ml. The final concentration of DMA and polyethoxylated castor oil is 10 percent. Dilutions for lower doses are made with saline so there is a decreasing proportion of organic solvents in the vehicle with decreasing dosage. This vehicle provides a soluble formulation. Formulations are prepared immediately prior to injection. The compound is administered ip on Days 1 through 5 (i.e. treatment is initiated 24 hrs after tumor inoculation). Each experiment includes three groups of 6 animals as untreated controls and animals treated with a positive control, cisplatin, at two dose levels. Animals are weighed as a group on Days 1, 5 and 9 and average weight change (Δ wt.) is used as a reflection of toxicity. Each experiment also includes an inoculum titration—groups of 8 mice inoculated ip with $10^5$ to $10^\circ$ P388 leukemia cells. The titration is used to calculate cell kill achieved by treatment with drugs. Animals are monitored daily for mortality and experiments are terminated after 45 days. The endpoint is median survival time (MST) and increase in lifespan (ILS) which is the percentage of increase in MST relative to untreated controls. Untreated controls inoculated ip with $10^6$ P388 leukemia cells generally survive for a median of 10 or 11 days. A drug is considered active if it produces 25 percent ILS.

A summary of the evaluation of a compound of Formula (I) in the in vivo ip P388 model is shown in the following Table A.

TABLE A

Formula (I)

$$(R)_2-P-A-P \overset{R}{\underset{\diagup}{\diagdown}} \overset{}{\underset{Au^\oplus}{\diagup}} A \quad X^-$$
$$(R)_2-P-A-P \underset{R}{\diagup}$$

| Compound Number | R | A | X | MTD[a] (mg/kg) | ILS (max)[b] (%) |
|---|---|---|---|---|---|
| 1 | phenyl | (CH$_2$)$_2$ | Cl | 3 | 40/65 |

[a]maximally tolerated dose for B62DF female mice on an ip qDX5 regimen.
[b]maximum increase in lifespan produced in mice bearing ip P388 leukemia (figures separated by slashes indicate data generated in separate experiments).

Based on the data set forth in Table A, a compound of Formula (I) showed significant antitumor activity in the in vivo ip P388 leukemia tumor assay.

The cytotoxic activity of Compound No. 1 of Table A was evaluated in vivo using B16 melanoma cells. In this system, groups of eight B6D2F$_1$ mice are inoculated ip with 0.5 ml of a 10% (w:v) brei of B15 melanoma prepared from pooled sc tumors excised at 14–21 days from C67B$_1$/6 donor mice. Daily treatment is begun 24 hours after tumor implantation and is continued daily for ten (10) days. The route of drug administration is ip. The mice are monitored daily for survival for sixty (60) days. Antitumor activity is assessed by prolongation of median survival time. An ILS of ≧25% indicates activity in this tumor model.

A summary of the results of the in vivo ip B16 melanoma assay is shown in Table B.

TABLE B

| Compound No.[a] | MTD (mg/kg)[b] | ILS (%)[c] |
|---|---|---|
| 1 | 2 | 37 |

[a]see Table A for structure.
[b]maximally tolerated dose for B6D2F$_1$ mice on an ip qD × 10 regimen.
[c]maximum increase in lifespan produced in mice bearing ip B16 melanoma.

Another chemosensitive tumor model is intraperitoneally (ip) implanted M5076 reticulum cell sarocma in mice. In this system B6D2F female mice are inoculated with 0.5 ml of a 10 percent (w:v) brei of M5076 prepared from pooled subcutaneous (sc) tumors excised at about 21 days from C57B1/6 donors. Drugs are administered ip. Daily treatment is begun 24 hours after implantation and is continued for ten days. The treatment regimen for M5076 is more prolonged than for P388 because of the slower growth rate and longer control survival time of the M5076 tumor. A drug is considered active in this tumor model if it produces ≧25% ILS. The antitumor activity of Compound No. 1 of Table A in the M5076 reticulum cell sarcoma tumor model is set forth in Table C.

TABLE C

| Compound No.[a] | MTD (mg/kg)[b] | ILS (MAX) (%)[c] |
|---|---|---|
| 1 | 2 | 38 |

[a]see Table A for structure
[b]maximally tolerated dose for B6D2F female mice on ip qD × 10 regimen
[c]maximum increase in lifespan produced in mice bearing ip M5076 reticulum cell sarcoma The pharmaceutical compositions of this invention comprise an effective tumor cell growth-inhibiting amount of a compound of Formula (I) and an inert pharmaceutically acceptable carrier or diluent. These compositions are prepared in dosage unit form appropriate for parenteral administration.

Compositions according to the invention for parenteral administration include sterile aqueous or non-aqueous solutions, suspensions or emulsions. The composition may be in the form of a solution of the active ingredient in a minimal volume of dimethylacetamide or ethanol, for example 5% v/v, brought up to volume with peanut oil or normal saline solution. Polyethoxylated castor oil, for example 2 to 5% v/v, may also be used to solubilize the active ingredient. In addition, the composition may be in the form of a slurry with, for example, hydroxypropyl cellulose or other suitable suspending agent. As an emulsifying agent, lecithin for example may be used. The composition may also be provided in the form of a sterile solid which can be dissolved in a sterile injectable medium immediately before use.

Freireich et al., *Cancer Chemo, Rept.*, 50, 219–244 (1966), compared the quantitative toxicity of 18 anticancer drugs in six species after correcting the data to a uniform schedule of treatment for five consecutive days. This analysis demonstrated that mouse, rat, dog, human, monkey and man have essentially the same maximum tolerated dose (MTD) when compared on a basis of mg/m$^2$ of body surface area. The study suggested that Phase I clinical trials could be safely initiated at a dose one-third the animal MTD. The mouse was as useful as any other species in this regard on which to base the calculation. The appropriate therapeutically effective dose for any compound of the invention can therefore be determined readily by those skilled in the art from simple experimentation with laboratory animals, perferably mice.

It will be appreciated that the actual preferred dosages of the compounds of Formula (I) used in the compositions of this invention will vary according to the particular compound being used, the particular composition formulated, the mode of administration and the particular site, host and disease being treated. The route of internal administration should be selected to ensure that an effective tumor cell growth-inhibiting amount of the compound of Formula (I) contacts the tumor. Optimal dosages for a given set of conditions can be ascertained by those skilled in the art using conventional dosage determination tests in view of the above experimental data. For parenteral administration the dose generally employed is from about 5 to about 20 mg/m$^2$ of body surface per day for one to five days, repeated about every fourth week for four courses of treatment.

The method for inhibiting the growth of animal tumor cells sensitive to a compound of Formula (I) in accordance with this invention comprises administering to a host animal afflicted with said tumor cells, an effective tumor cell growth-inhibiting amount of a compound of Formula (I). As described above, during the course of treatment the active ingredient will be administered parenterally in an amount selected from about 300 mg to about 1000 mg.

EXAMPLES

The following examples illustrate the chemical preparation of several compounds of Formula (I) which are used in the compositions and methods of this invention and as such are not to be construed as limiting the scope thereof. All temperatures are in degrees Centigrade.

EXAMPLE 1

Chloro[1,1,4,7,10,10-hexaphenyl-1,4,7,10-tetraphosphodecane-P$^1$, P$^4$, P$^7$, P$^{10}$]gold(I)

Chloroauric acid tetrahydrate (1.87 g, 4.54 mmol) in water (20 ml) was reduced upon addition of thiodiglycol (3.0 g, 24.6 mmole) in methanol (60 ml)/water (20 ml) at 0°. 1,1,4,7,10,10-hexaphenyl-1,4,7,10-tetraphosphodecane (TETRAPHOS-I) (0.76 g, 1.13 mmole), obtained from Strem Chemicals, Inc., Newburyport, Mass., in chloroform (60 ml)/methanol (20 ml) was added, and the mixture was stirred for several hours. The resulting precipitate was collected, dissolved in methylene chloride, hexane was added and the solution was cooled. Collection of successive crops gave 1.35 g (84%) of μ-[1,1,4,7,10,10-hexaphenyl-1,4,7,10-tetraphosphodecane]tetrakis[chlorogold(I)], which had a melting point (m.p.) of 184°–186°.

To a suspension of μ-[1,1,4,7,10,10-hexaphenyl-1,4,7,10-tetraphosphodecane]tetrakis[chlorogold(I)] (0.5 g, 0.3 mmole), prepared as described above, in chloroform (25 ml) was added TETRAPHOS-I (0.063 g, 0.94 mmole) in chloroform (25 ml). After stirring the mixture for 18 hours at ambient temperature, the solvent was evaporated and the residue dissolved in methanol, filtered, ethyl ether was added, and the mixture was cooled. The resulting precipitate was collected and dried to give 0.37 g (33%) of the named product as a hydrate, m.p. 241°–242°.

EXAMPLE 2

Using the procedure of Example 1 to react the appropriate tetraphos ligand of Formula (IA) with the appropriate tetraphos-gold complex of Formula (IB), prepared according to the procedure of Example 1 by using the appropriate bromo- or chloroauric acid hydrate, the following compounds of Formula (I) wherein X is chloro or bromo are prepared; or by reacting the appropriate compound of Formula (I), wherein X is chloro, with sodium bromide in an appropriate organic solvent, such as aqueous ethanol or DMF, the following compounds of Formula (I) wherein X is bromo are prepared; and by reacting the appropriate compound of Formula (I), wherein X is chloro or bromo, with sodium iodide in an appropriate organic solvent, such as acetone, the following compounds of Formula (I) wherein X is iodo are prepared:

a. Chloro[1,1,3,5,7,7-hexaphenyl-1,3,5,7-tetraphosphoheptane-P$^1$, P$^3$, P$^5$, P$^7$]gold(I)
b. Chloro[1,1,5,9,13,13-hexaphenyl-1,5,9,13-tetraphosphotridecane-P$^1$, P$^5$, P$^9$, P$^{13}$]gold(I)
c. Chloro[1,1,6,11,16,16-hexaphenyl-1,6,11,16-tetraphosphohexadecane-P$^1$, P$^5$, P$^9$, P$^{16}$]gold(I)
d. Chloro[1,1,7,13,19,19-hexaphenyl-1,7,13,19-tetraphosphononadecane-P$^1$, P$^7$, P$^{13}$, P$^{19}$]gold(I)
e. Chloro[1,1,8,15,22,22-hexaphenyl-1,8,15,22-tetraphosphodocosane-P$^1$, P$^8$, P$^{15}$, P$^{22}$]gold(I)
f. Bromo[1,1,4,7,10,10-hexaphenyl-1,4,7,10-tetraphosphodecane-P$^1$, P$^4$, P$^7$, P$^{10}$]gold(I)
g. Iodo[1,1,4,7,10,10-hexaphenyl-1,4,7,10-tetraphosphodecane-P$^1$, P$^4$, P$^7$, P$^{10}$]gold(I)

EXAMPLE 3

As a specific embodiment of a composition of this invention, an active ingredient, such as one part of the compound of Example 1, is dissolved in 5 parts of dimethylacetamide and 5 parts of polyethoxylated castor oil and then normal saline solution qs, and is administered parenterally in one dose of 5 mg/m$^2$ to a host animal afflicted with tumor cells sensitive to that compound.

What is claimed is:

1. A parenterally pharmaceutical composition which comprises an effective tumor cell growth-inhibiting amount of an active ingredient and an inert, pharmaceutically acceptable carrier or diluent, wherein said composition is useful for inhibiting the growth of animal tumor cells sensitive to the active ingredient, and wherein the active ingredient is a compound of the formula:

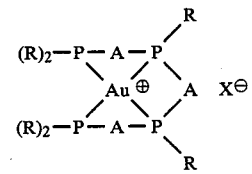

wherein
R is the same and is phenyl;
A is the same and is a straight or branched alkanediyl chain of from one to six carbon atoms; and
X is halo.

2. The composition of claim 1 wherein A is ethane-1,2-diyl.

3. The composition of claim 2 wherein X is chloro.

4. The composition of claim 1 wherein the parenteral dosage unit is adapted to administer from about 5 to about 20 mg/m² of body surface.

5. A method of inhibiting the growth of animal tumor cells sensitive to a compound of the formula:

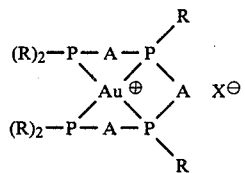

wherein
R is the same and is phenyl;
A is the same and is a straight or branched alkanediyl chain of from one to six carbon atoms; and
X is halo;

which comprises parenterally administering to an animal afflicted with said tumor cells, an effective, tumor cell growth-inhibiting amount of said compound.

6. The method according to claim 5 wherein A is ethane-1,2-diyl.

7. The method according to claim 6 wherein X is chloro.

8. The method according to claim 5 wherein the administration is parenteral and the amount is selected from a unit dose range of from about 5 to about 20 mg/m² of body surface administered per dose for one to five days.

9. The method according to claim 8 wherein the administration is repeated about every fourth week for four courses of treatment.

10. The method according to claim 9 wherein during the course of treatment the amount administered is from about 300 to about 1000 mg.

* * * * *